(12) United States Patent
Towns et al.

(10) Patent No.: US 8,860,007 B2
(45) Date of Patent: *Oct. 14, 2014

(54) ARYL-SUBSTITUTED POLYINDENOFLUORENES FOR USE IN ORGANIC ELECTROLUMINISCENT DEVICES

(75) Inventors: Carl Towns, Essex (GB); Ian Rees, Cambridge (GB); Ilaria Grizzi, Cambridge (GB); Mary Mckiernan, Cambridgeshire (GB); Paul Wallace, Hertfordshire (GB); Thomas Pounds, Cambridge (GB); Clare Foden, Cambridge (GB); Sophie Heidenhain, Cambridgeshire (GB)

(73) Assignee: Merck Patent GmbH (DE)

( * ) Notice: Subject to any disclaimer, the term of this patent is extended or adjusted under 35 U.S.C. 154(b) by 2589 days.

This patent is subject to a terminal disclaimer.

(21) Appl. No.: 10/533,920

(22) PCT Filed: Nov. 6, 2003

(86) PCT No.: PCT/EP03/12369
§ 371 (c)(1),
(2), (4) Date: Jun. 7, 2005

(87) PCT Pub. No.: WO2004/041901
PCT Pub. Date: May 21, 2004

(65) Prior Publication Data
US 2006/0046092 A1    Mar. 2, 2006

(30) Foreign Application Priority Data
Nov. 8, 2002  (GB) .................... 0226010.7

(51) Int. Cl.
| | | |
|---|---|---|
| C08G 61/02 | (2006.01) | |
| C08G 61/12 | (2006.01) | |
| C09K 11/06 | (2006.01) | |
| H01L 51/30 | (2006.01) | |
| H01L 51/46 | (2006.01) | |
| H01L 51/54 | (2006.01) | |
| C07C 13/70 | (2006.01) | |
| C09B 69/10 | (2006.01) | |
| C07F 5/02 | (2006.01) | |
| H05B 33/14 | (2006.01) | |
| H01L 51/00 | (2006.01) | |
| H01L 51/50 | (2006.01) | |

(52) U.S. Cl.
CPC ............ *H05B 33/14* (2013.01); *C07C 13/70* (2013.01); *C09K 2211/1416* (2013.01); *C09B 69/109* (2013.01); *Y02E 10/549* (2013.01); *H01L 51/0039* (2013.01); *H01L 51/0035* (2013.01); *C08G 61/02* (2013.01); *H01L 51/0059* (2013.01); *C09K 11/06* (2013.01); *C07F 5/025* (2013.01); *H01L 51/0043* (2013.01); *H01L 51/50* (2013.01); *Y10S 428/917* (2013.01)
USPC ...... 257/40; 257/E51.037; 313/504; 428/917; 528/8; 528/394; 528/396; 528/397

(58) Field of Classification Search
USPC .............................. 428/690, 917; 427/58, 66; 313/502–509; 257/40, 88–103, 257/E51.001–E51.052; 252/301.16–301.35
See application file for complete search history.

(56) References Cited

U.S. PATENT DOCUMENTS

| | | | |
|---|---|---|---|
| 5,621,131 A | 4/1997 | Kreuder et al. | |
| 5,856,434 A * | 1/1999 | Stern et al. | 528/402 |
| 6,353,072 B1 * | 3/2002 | Towns et al. | 528/4 |
| 6,353,083 B1 * | 3/2002 | Inbasekaran et al. | 528/295 |
| 6,479,172 B2 * | 11/2002 | Hu et al. | 428/690 |
| 6,653,438 B1 | 11/2003 | Spreitzer et al. | |
| 2004/0178414 A1 * | 9/2004 | Frey et al. | 257/79 |
| 2005/0038223 A1 | 2/2005 | Becker et al. | |
| 2007/0252139 A1 * | 11/2007 | Mckiernan et al. | 257/40 |

FOREIGN PATENT DOCUMENTS

| | | |
|---|---|---|
| DE | 198 46 767 | 4/2000 |
| DE | 102 41 814 | 3/2004 |
| DE | 103 37 077 | 3/2005 |
| EP | 0 707 020 | 4/1996 |
| EP | 0 842 208 | 5/1998 |
| EP | 0 949 850 | 10/1999 |
| WO | WO-90/13148 | 11/1990 |
| WO | WO-92/03490 | 3/1992 |
| WO | WO-97/05184 | 2/1997 |
| WO | WO-97/42666 | 11/1997 |
| WO | WO-98/05187 | 2/1998 |
| WO | WO-98/06773 | 2/1998 |
| WO | WO-99/48160 | 9/1999 |
| WO | WO-99/54385 | 10/1999 |
| WO | WO-00/22026 | 4/2000 |
| WO | WO-00/46321 | 8/2000 |
| WO | WO-00/53656 | 9/2000 |

(Continued)

OTHER PUBLICATIONS

Peng et al., "Novel polymers for light emitting diodes", Acta Polymerica, vol. 49, pp. 244-247 (1998).*

(Continued)

*Primary Examiner* — Marie R. Yamnitzky
(74) *Attorney, Agent, or Firm* — Drinker Biddle & Reath LLP

(57) ABSTRACT

The invention relates to organic semiconductive polymers comprising a new backbone system, monomers for the preparation of such polymers, methods for the preparation of such polymers and the use of such polymers in organic optoelectronic devices.

18 Claims, No Drawings

(56) References Cited

FOREIGN PATENT DOCUMENTS

| WO | WO-00/55927 | | 9/2000 |
|---|---|---|---|
| WO | WO 00/79617 | * | 12/2000 |
| WO | WO 00/42331 | * | 6/2001 |
| WO | WO-01/49769 | | 7/2001 |
| WO | WO-02/23579 | | 3/2002 |
| WO | WO 02/095841 A2 | * | 11/2002 |
| WO | WO-03/020790 | | 3/2003 |

OTHER PUBLICATIONS

Liu et al., "Effects of thermal annealing on the performance of polymer light emitting diodes", Journal of Applied Physics 91(3), pp. 1595-1600 (Feb. 2002).*

Setayesh, S. et al., "Bridging the Gap Between Polyfluorene and Ladder-Poly-$p$-phenylene: Synthesis and Characterization of Poly-2, 8-indenofluorene", Macromolecules (2000), 33, 2016-2020.

Ego, C. et al., "Triphenylamine-Substituted Polyfluorene—A Stable Blue-Emitter with Improved Charge Injection for Light-Emitting Diodes", Advanced Materials (2002), 14, No. 11, pp. 809-811.

Marsitzky, D. et al., "Poly-2,8-(indenofluorene-co-anthracene)—A Colorfast Blue-Light-Emitting Random Copolymer", Advanced Materials (2001), 13, No. 14, pp. 1096-1099.

Setayesh, S. et al., "Polyfluorenes with Polyphenylene Dendron Side Chains: Toward Non-Aggregating, Light-Emitting Polymers", J. Am. Chem. Soc. (2001), 123, pp. 946-953.

Jacob, J. et al., "Poly(tetraarylindenofluorene)s: New Stable Blue-Emitting Polymers", Macromolecules (2003), 36, pp. 8240-8245.

* cited by examiner

ARYL-SUBSTITUTED POLYINDENOFLUORENES FOR USE IN ORGANIC ELECTROLUMINISCENT DEVICES

RELATED APPLICATIONS

This application is a national stage application (under 35 U.S.C. 371) of PCT/EP2003/012369 filed Nov. 3, 2003 which claims benefit to Great Britain application 0226010.7 filed Nov. 8, 2002.

FIELD OF THE INVENTION

The present invention relates to organic semiconductive polymers comprising aryl substituted trans-indenofluorene repeat units, monomers for the preparation of such polymers, methods for the preparation of such polymers and the use of such polymers in organic optoelectronic devices.

BRIEF DESCRIPTION OF THE PRIOR ART

Semiconductive organic polymers have been known for several decades. During the past ten years they have found increasing application as transistors and in the field of optoelectronic devices including organic photovoltaic devices (in particular solar cells), organic photodetectors and electroluminescent devices, also known as polymeric light emitting devices, see for example WO 90/13148.

A polymeric light emitting device comprises a negative charge carrier injecting electrode, a positive charge carrier injecting electrode and a layer of polymeric light emitting material situated between the two electrodes. Application of a voltage between the two electrodes causes positive charge carriers, known as holes, to be injected from the positive charge injecting electrode and negative charge carriers, electrons, to be injected from the negative charge carrier injecting electrode. The holes and electrons combine in the layer of polymeric light emitting material to form an exciton which decays emitting light. The electroluminescent device may also comprise further layers for the transport of charge carriers from the electrodes to the layer of light emitting polymers, alternatively the light emitting polymer itself may incorporate charge transporting units in addition to light emissive units.

The nature of the polymeric material used in electroluminescent devices is critical to the performance of the device. Materials used include poly(phenylenevinylenes), as disclosed in WO 90/13148, polyfluorenes, as disclosed in WO 97/05184 and poly(arylamines) as disclosed in WO 98/06773. Copolymers and blends of polymers have been found to be useful in such devices, as disclosed in WO 92/03490, WO 99/54385, WO 00/55927 and WO 99/48160. Poly(arylamines) have been disclosed in which the aromatic groups may comprise heteroaromatic moieties such as triazine as disclosed in WO 01/49769. In copolymers and blends of polymers different monomer units are used to provide different functions in the device, namely electron transport, hole transport and light emission.

In particular chains of fluorene repeat units, such as homopolymers or block copolymers comprising dialkylfluorene repeat units, may be used as electron transporting materials. In addition to their electron transporting properties, polyfluorenes have the advantages of being soluble in conventional organic solvents and have good film forming properties. Furthermore, fluorene monomers are amenable to Yamamoto polymerisation or Suzuki polymerisation which enables a high degree of control over the regioregularity of the resultant polymer.

One example of a polyfluorene based polymer is a blue electroluminescent polymer of formula (a) disclosed in WO 00/55927:

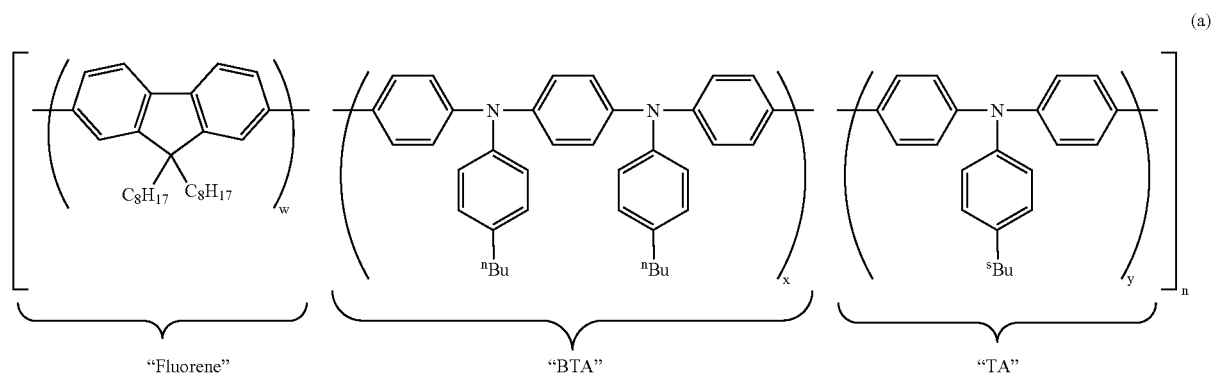

(a)

wherein w+x+y=1, w≥0.5, 0≤x+y≤0.5 and n≥2.

In this polymer, chains of dioctylfluorene, denoted as Fluorene, function as the electron transport material; the triphenylamine, denoted as TA, functions as the hole transport material and the bis(diphenylamino)benzene derivative, denoted as BTA, functions as the emissive material.

There are a number of disadvantages associated with fluorene based polymers which have led to a search for alternative electron transporting and light emitting units. These disadvantages include the limited hole transporting ability of the fluorene units, the tendency of fluorene units to aggregate and the fact that when blue light emission occurs from fluorene based polymers the emission does not occur in the region of the electromagnetic spectrum in which the human eye is most sensitive.

In an effort to provide alternatives to fluorene based polymers which do not show these disadvantages, light emitting polymers comprising alkyl substituted trans-indenofluorene units (one example is shown below) have been described by S. Setayesh et al. (Macromolecules, 2000, 33, 2016) and others.

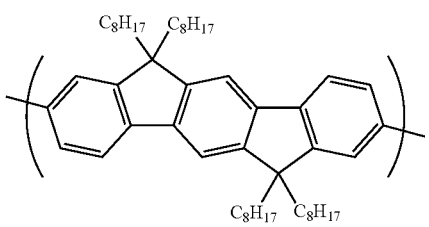

These polymers are formed by polymerisation of the corresponding dibromo-monomer in the presence of a nickel catalyst. However, these homopolymers generally show the same disadvantages as described above, namely the tendency to aggregate. Luminescence occurred from aggregates or excimers, resulting in a broad emission band with an emission maximum in the green region. Therefore, these homopolymers are not useful for the generation of blue light. Marsitzky et al. (Advanced Materials, 2001, 13, 1096-1099) describe the supression of aggregate emission by copolymerising tetraoctyl substituted trans-indenofluorene with anthracene resulting in a blue emission. However, after storage at room temperature, the PL efficiency decreases which is attributed to morphology changes facilitating the formation of small amounts of excimer/aggregates. It is therefore obvious that these trans-indenofluorenes are not useful for the stable generation of blue light.

SUMMARY OF THE INVENTION

The present inventors have found that poly(trans-indenofluorenes) that are substituted with at least one aromatic or heteroaromatic group in the 6 and/or 12 position do not show the disadvantages described above. They are therefore suitable for the use in blue light emitting devices. They have further found that these poly(trans-indenofluorenes) are more stable to hole transport than polyfluorenes. In order to provide a range of poly(trans-indenofluorenes) with wider application in light emitting devices the present inventors have found that by providing at least one aryl or heteroaryl substituent on the trans-indenofluorene unit it is possible to provide trans-indenofluorene units with a higher electron affinity and therefore improved electron injecting and transporting properties. A further advantage of such aryl substituted trans-indenofluorene units is that polymers comprising these units have a higher Tg (glass transition temperature) and are therefore more stable and provide longer lived light emitting devices.

Accordingly, in a first aspect the invention provides polymers comprising optionally substituted first repeat units of formula (I):

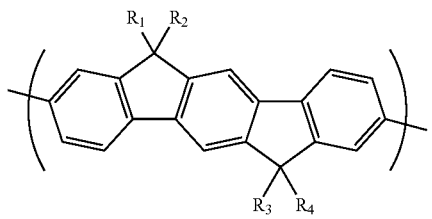

wherein $R_1$, $R_2$, $R_3$ and $R_4$ are selected from hydrogen, alkyl, alkyloxy, aryl, aryloxy, heteroaryl or heteroaryloxy groups, and $R_1$ and $R_2$ and/or $R_3$ and $R_4$ may be linked to form a monocyclic or polycyclic, aliphatic or aromatic ring system, provided that at least one of $R_1$, $R_2$, $R_3$ and $R_4$ comprises an aryl or heteroaryl group.

Preferably, alkyl is $C_1$-$C_{20}$-alkyl which can be each straight-chain, branched or cyclic, where one or more non-adjacent CH2 groups may be replaced by oxygen, sulphur, —CO—, —COO—, —O—CO—, $NR^{10}$—, —$(NR^{11}R^{12})^+$-$A^-$ or $CONR^{13}$—, in particular preferred methyl, ethyl, n-propyl, i-propyl, n-butyl, i-butyl, s-butyl, t-butyl, n-pentyl, s-pentyl, cyclopentyl, n-hexyl, cyclohexyl, n-octyl or cyclooctyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, arylalkyl is $C_7$-$C_{20}$-arylalkyl, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred o-tolyl, m-tolyl, p-tolyl, 2,6-dimethylphenyl, 2,6-diethylphenyl, 2,6-di-i-propylphenyl, 2,6-di-t-butylphenyl, o-t-butylphenyl, m-t-butylphenyl or p-t-butylphenyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryl is $C_7$-$C_{20}$-alkylaryl, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred benzyl, ethylphenyl, propylphenyl, diphenylmethyl, triphenylmethyl or naphthalinylmethyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryl is $C_6$-$C_{20}$-aryl, in particular preferred phenyl, biphenyl, naphthyl, anthracenyl, triphenylenyl, [1,1';3', 1"]terphenyl-2'-yl, binaphthyl or phenanthreny.I Preferably, heteroaryl is $C_5$-$C_{20}$-heteroaryl, in particular preferred 2-pyridyl, 3-pyridyl, 4-pyridyl, chinolinyl, isochinolinyl, acridinyl, benzochinolinyl or benzoisochinolinyl.

Preferably, alkyloxy is $C_1$-$C_{20}$-alkyloxy, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred methoxy, ethoxy, n-propoxy, i-propoxy, n-butoxy, i-butoxy, s-butoxy or t-butoxy, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryloxy is $C_6$-$C_{20}$-Aryloxy, in particular preferred phenoxy, naphthoxy, biphenyloxy, anthracenyloxy or phenanthrenyloxy.

Preferably, arylalkyloxy is $C_7$-$C_{20}$-arylalkyloxy where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryloxy is $C_7$-$C_{20}$-alkylaryloxy, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylthio is $C_1$-$C_{20}$-alkylthio where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$— and $R^{10}$, $R^{11}$, $R^{12}$, $R^{13}$ are identical or different and are hydrogen or an aliphatic or aromatic hydrocarbon radical having 1 to 20 carbon atoms.

In a preferred embodiment at least two of $R_1$, $R_2$, $R_3$ and $R_4$ comprise an aryl or heteroaryl group. Alternatively at least three of $R_1$, $R_2$, $R_3$ and $R_4$ comprise an aryl or heteroaryl group or each of $R_1$, $R_2$, $R_3$ and $R_4$ may comprise an aryl or heteroaryl group.

In a particularly preferred embodiment $R_1$ and $R_2$ comprise an aryl or heteroaryl group and $R_3$ and $R_4$ comprise an alkyl group.

Suitable aryl groups include phenyl, substituted phenyl, in particular alkyl substituted phenyl groups such as 4-octyl-phenyl and 4-tert-butyl-phenyl, fluoroalkyl substituted phenyls such as 4-(trifluoromethyl)phenyl, alkoxy substituted phenyl, such as 4-(2-ethylhexyloxy)phenyl and 4-methoxyphenyl, fluorinated phenyls, such as perfluorophenyls and 4-fluorophenyl and aryl substituted phenyls such as 4-(phenyl)phenyl. Suitable heteroaryl groups include pyridine, triazine, thiophene, pyrrole and furan, the heteroaryl groups may be substituted with alkyl, alkoxy, fluoro, fluoroalkyl, aryl or heteroaryl substituents.

Where one of $R_1$, $R_2$, $R_3$ and $R_4$ comprises an alkyl group suitable alkyl groups include octyl, tert-butyl, methyl, hexyl, perfluorooctyl or perfluorohexyl. Where one of $R_1$, $R_2$, $R_3$ and $R_4$ comprises an alkyl group the most preferred alkyl group is octyl.

It is particularly advantageous if the aryl group comprises an optionally substituted phenyl group. 4-Octylphenyl and 4-tert-butyl-phenyl substituents are preferred.

Where $R_1$ and $R_2$ comprise an aryl or heteroaryl group and $R_3$ and $R_4$ comprise an alkyl group it is preferred that $R_1$ and $R_2$ are selected group 4-octylphenyl and 4-tert-butyl-phenyl substituents and that $R_3$ and $R_4$ comprises octyl substituents.

The polymers of the present invention may be homopolymers or copolymers. Suitable copolymers may comprise two, three or more distinct monomer-units. In a preferred embodiment the polymer of the present invention comprises a second repeat unit, preferably this repeat unit comprises a triarylamine or a heteroaromatic. Preferred triarylamine comonomers include N,N-di(4-phenyl)-N-(4-sec-butylphenyl)amine ("TA") and bis[N-(4-phenyl)-N-(4-n-butylphenyl)]-phenylene-1,4-diamine ("BTA").

The polymers of the present invention may be prepared by any suitable method. In a second aspect, the invention provides a monomer comprising an optionally substituted compound of formula (II):

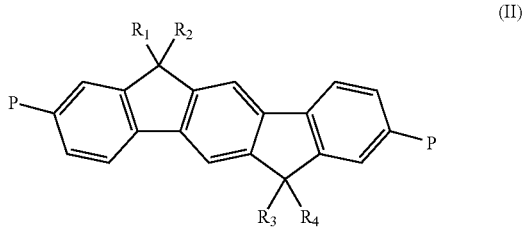

(II)

wherein each P independently represents a polymerisable group and $R_1$, $R_2$, $R_3$ and $R_4$ are as defined above. Preferably each P is independently selected from a reactive boron derivative group selected from a boronic acid group, a boronic ester group and a borane group; a reactive halide group; or a moiety of formula —O—SO$_2$—Z wherein Z is selected from the group consisting of alkyl and aryl, each being optionally substituted.

The polymers of the present invention are suitably prepared by aryl-aryl coupling such as Yamamoto coupling or Suzuki coupling, Suzuki coupling is preferred.

Accordingly, in a third aspect the invention provides a process for preparing a polymer comprising a step of reacting a first monomer as described in the second aspect of the invention and a second monomer that may be the same or different from the first monomer under conditions so as to polymerise the monomers.

This process preferably comprises polymerising in a reaction mixture:

(a) a monomer as described in the second aspect of the invention wherein each P is a boron derivative functional group selected from a boronic acid group, a boronic ester group and a borane group, and an aromatic monomer having at least two reactive functional groups independently selected from halides or a moiety of formula —O—SO$_2$—Z; or (b) a monomer as described in the second aspect of the invention wherein each P is independently selected from the group consisting of reactive halide functional groups and moieties of formula —O—SO$_2$—Z, and an aromatic monomer having at least two boron derivative functional groups selected from boronic acid groups, boronic ester groups and borane groups; or (c) a monomer as described in the second aspect of the invention wherein one P is a reactive halide functional group or a moiety of formula —OSO$_2$—Z and one. P is a boron derivative functional group selected from a boronic acid group, a boronic ester group and a borane group, wherein Z is selected from the group consisting of optionally substituted alkyl and aryl and the reaction mixture comprises a catalytic amount of a catalyst suitable for catalysing the polymerisation of the aromatic monomers, and a base in an amount sufficient to convert the boron derivative functional groups into boronate anionic groups without wishing to be bound to a specific theory.

In a fourth aspect, the invention provides an optical device comprising a polymer according to the first aspect of the invention. Preferably, the optical device is an organic light emitting device. In particular the polymers of the present invention may function as the electron transporting or light emissive components of an organic light emitting device.

In a fifth aspect, the invention provides a switching device comprising a polymer according to the first aspect of the invention.

Preferably, the switching device is a field effect transistor comprising an insulator having a first side and a second side; a gate electrode located on the first side of the insulator; an oligomer or polymer according to the first aspect of the invention located on the second side of the insulator; and a drain electrode and a source electrode located on the oligomer or polymer.

In a sixth aspect, the invention provides an integrated circuit comprising a field effect transistor according to the fifth aspect of the invention.

In a seventh aspect, the invention provides a photovoltaic cell comprising a polymer according to the first aspect of the invention.

In a eighth aspect, the invention provides a monomer comprising an optionally substituted repeat unit of formula (III):

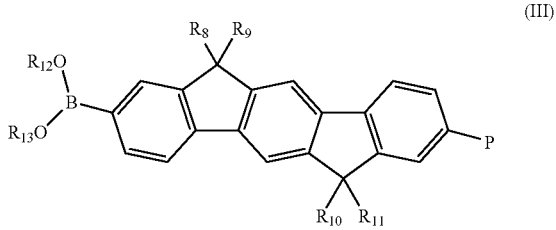

(III)

wherein $R_8$, $R_9$, $R_{10}$, $R_{11}$, $R_{12}$ and $R_{13}$ are the same or different and independently represent hydrogen or a substituent as defined for $R_1$-$R_4$; one or more of the pairs of $R_8$ and $R_9$, $R_{10}$ and $R_{11}$ or $R_{12}$ and $R_{13}$ may be linked to form a monocyclic or polycyclic, aliphatic or aromatic ring system; and P is as described in the second aspect of the invention.

Preferably, $R_8$, $R_9$, $R_{10}$ and $R_{11}$ are independently selected from the group consisting of optionally substituted alkyl, alkyoxy, aryl, aryloxy, heteroaryl or heteroaryloxy.

Preferably, P is selected from the group consisting of reactive halide functional groups, a monovalent unit of formula —$OSO_2Z$ or a monovalent unit of formula —$B(OR_{14})(OR_{15})$ wherein $R_{14}$ and $R_{15}$ are the same or different and independently represent hydrogen or a substituent as defined for $R_{12}$ and $R_{13}$ and may be linked to form a ring; and Z is as described in the third aspect of the invention.

Preferably, $R_{12}$, $R_{13}$, $R_{14}$ and $R_{15}$ are the same or different and are selected from the group consisting of hydrogen and optionally substituted alkyl.

Preferably, $R_{12}$ and $R_{13}$ and/or $R_{14}$ and $R_{15}$ are linked to form an optionally substituted ethylene group.

In an ninth aspect the invention provides a process for preparing a polymer which comprises polymerising in a reaction mixture:

(a) a monomer according to the seventh aspect of the invention wherein P is a group of formula —$B(OR_{14})(OR_{15})$, and an aromatic monomer having at least two reactive functional groups independently selected from halide or moieties of formula —O—$SO_2$—Z; or (b) a monomer according to the seventh aspect of the invention wherein P is a reactive halide functional group or a moiety of formula —O—$SO_2$—Z, wherein the reaction mixture comprises a catalytic amount of a catalyst suitable for catalysing the polymerisation of the aromatic monomers, and a base in an amount sufficient to convert the boron derivative functional groups into boronate anionic groups without wishing to be bound to a specific theory.

DETAILED DESCRIPTION OF THE INVENTION

Examples of repeat units according to the invention include the following:

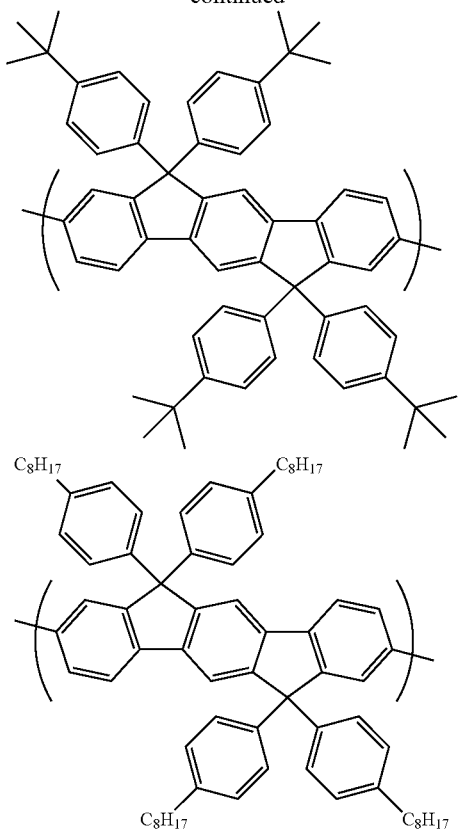

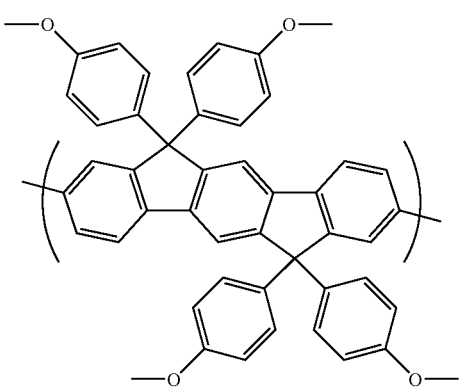

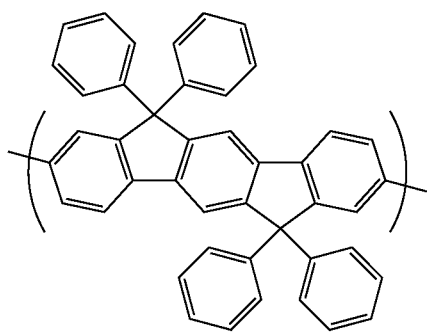

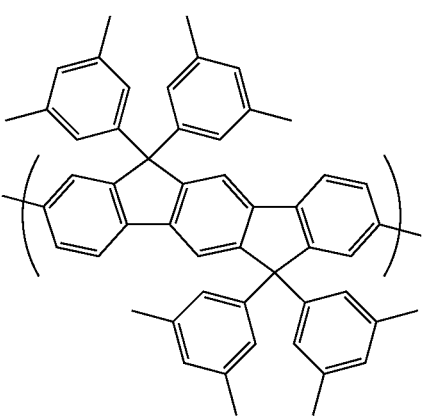

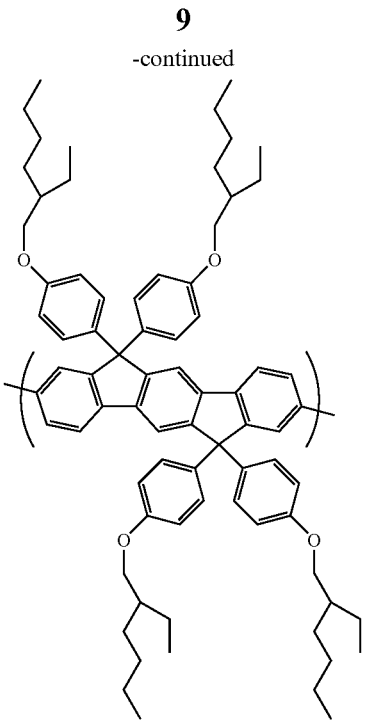

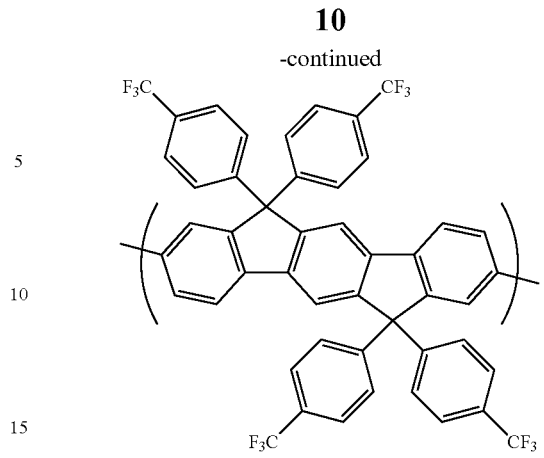

The aryl groups may be substituted with other aryl groups such as phenyl and substituted phenyl groups, as shown by the repeat units below:

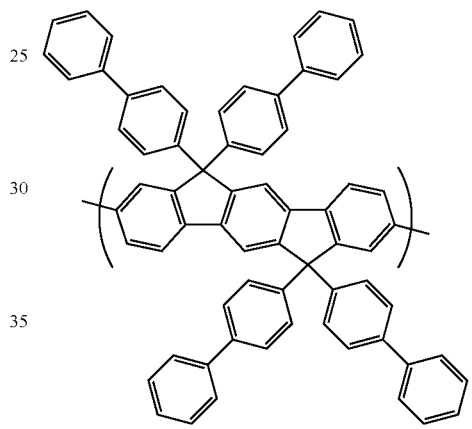

Substitution of the aryl groups with one or more alkyl chains comprising 4 to 12 carbon atoms has been found to improve the solubility of the polymers and also to limit aggregation of the polymer chains.

The aryl groups may also be substituted with fluoro or fluoroalkyl groups. In particular long chain perfluoroalkyl substitutents are considered to reduce aggregation of the polymer chains. A further advantage of fluoro and fluoroalkyl substituted aryl groups is that the electron withdrawing properties of these groups increases the LUMO of the polymer and so enables more efficient electron injection into the polymer. Examples of fluorine substituted repeat units include:

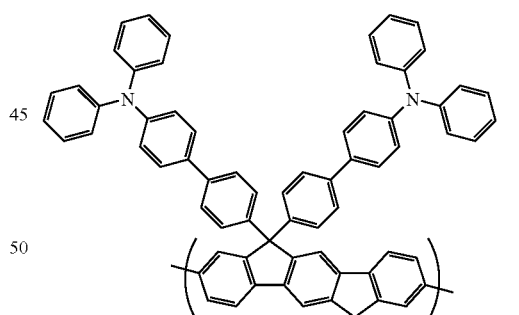

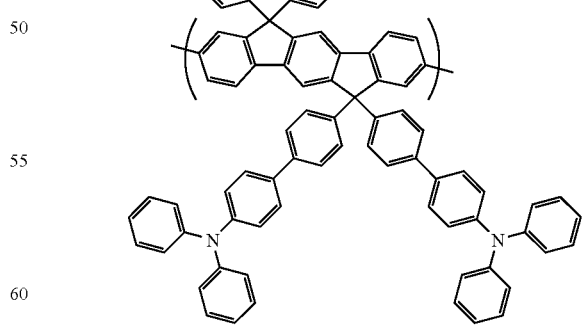

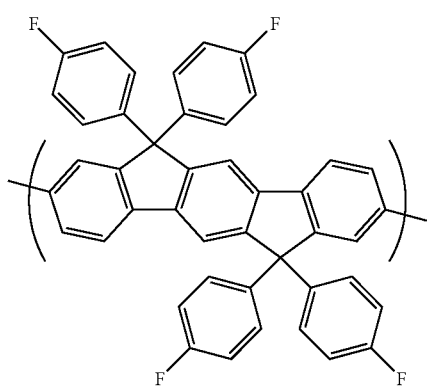

The repeat units may also be substituted with heteroaryl groups, in particular substituents based on pyridine, triazine and thiophene are considered to be useful:

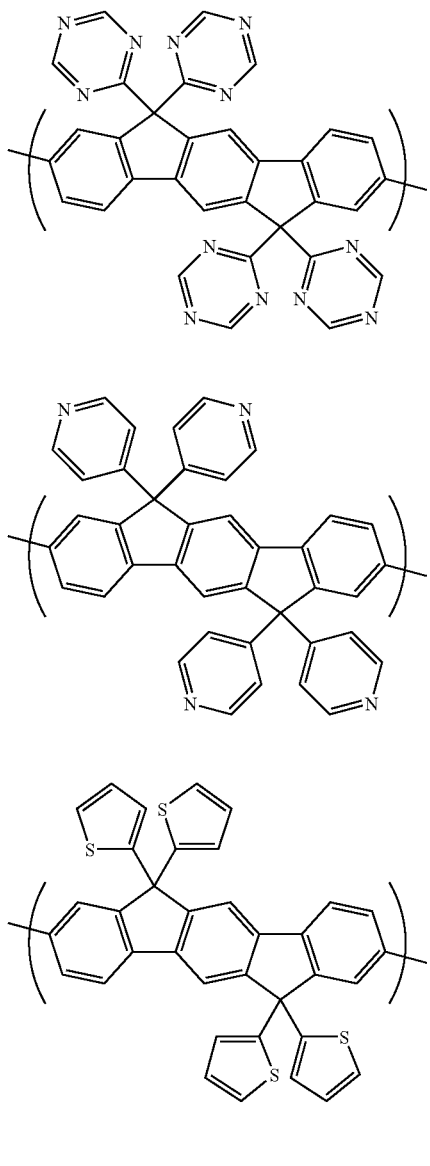

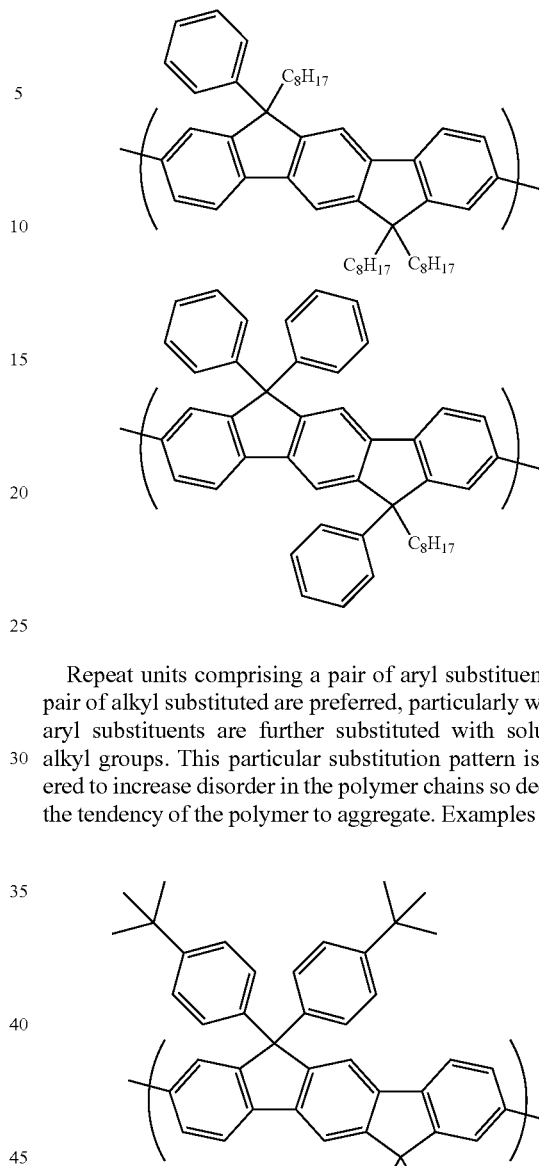

Repeat units comprising a pair of aryl substituents and a pair of alkyl substituted are preferred, particularly where the aryl substituents are further substituted with solubilising alkyl groups. This particular substitution pattern is considered to increase disorder in the polymer chains so decreasing the tendency of the polymer to aggregate. Examples include:

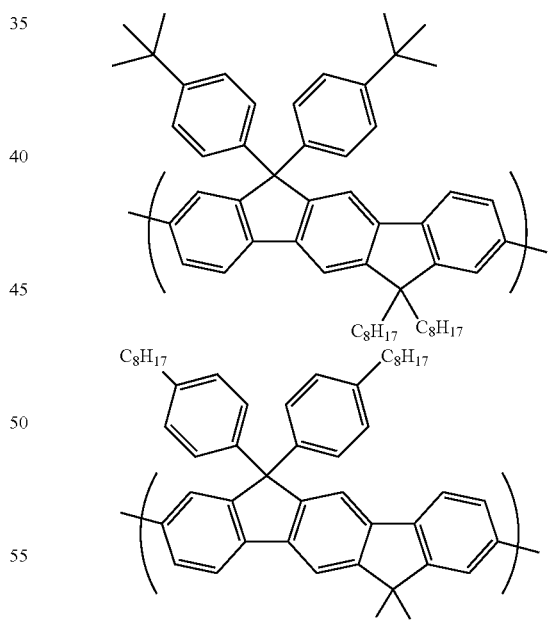

The polymers of the present invention may also comprise repeat units where the substituents $R_1$, $R_2$, $R_3$ and $R_4$ are not identical. For example $R_1$ and $R_2$ may comprise aryl substituents and $R_3$ and $R_4$ alkyl substituents, as shown below:

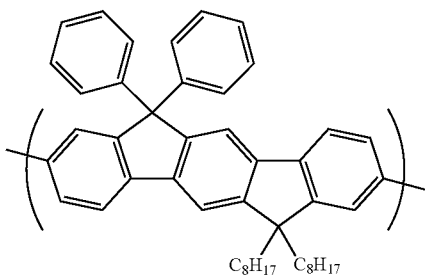

Alternatively the repeat units may comprise three aryl substituents and a single alkyl substituent or vice-versa, examples of such repeat units include:

The aromatic groups in the main chain of the polymer may themselves be substituted, for example they may be fluorinated. It is preferred that any such substituent comprises fewer than four carbon atoms since larger substituents cause twisting along the polymer chain and so reduce conjugation along the polymer chain giving the polymer less desirable electronic properties.

Alternatively, two or more of $R_1$, $R_2$, $R_3$ and $R_4$ may be different aryls, which may be formed by methods disclosed in WO 00/22026 and DE 19846767. Examples of such repeat units include the following:

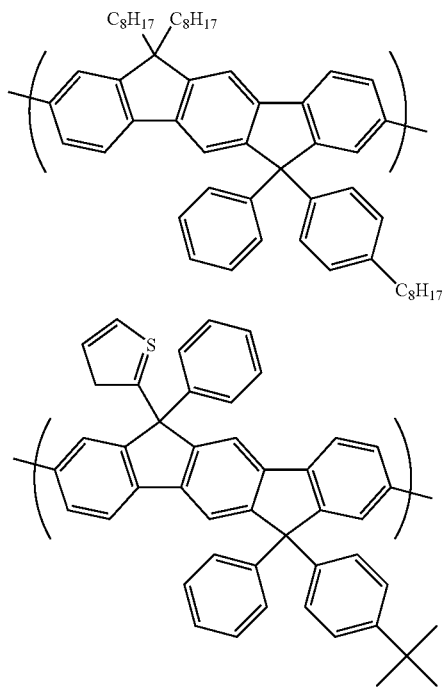

The groups $R_1$ and $R_2$ and/or $R_3$ and $R_4$ as described above may be linked to form a ring. Examples of such repeat units include the following:

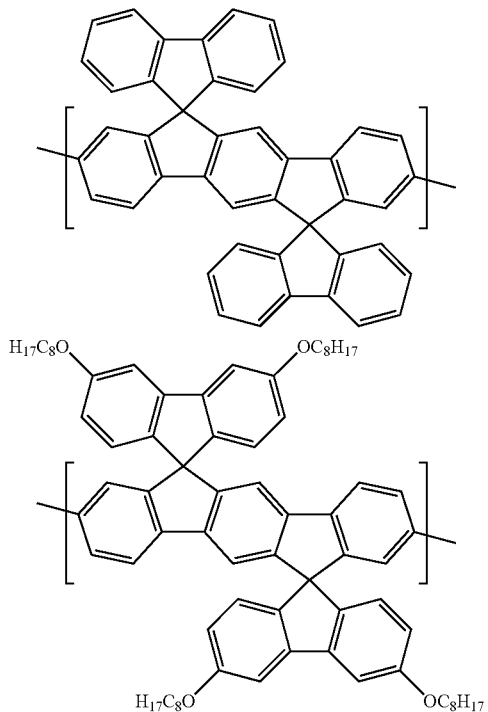

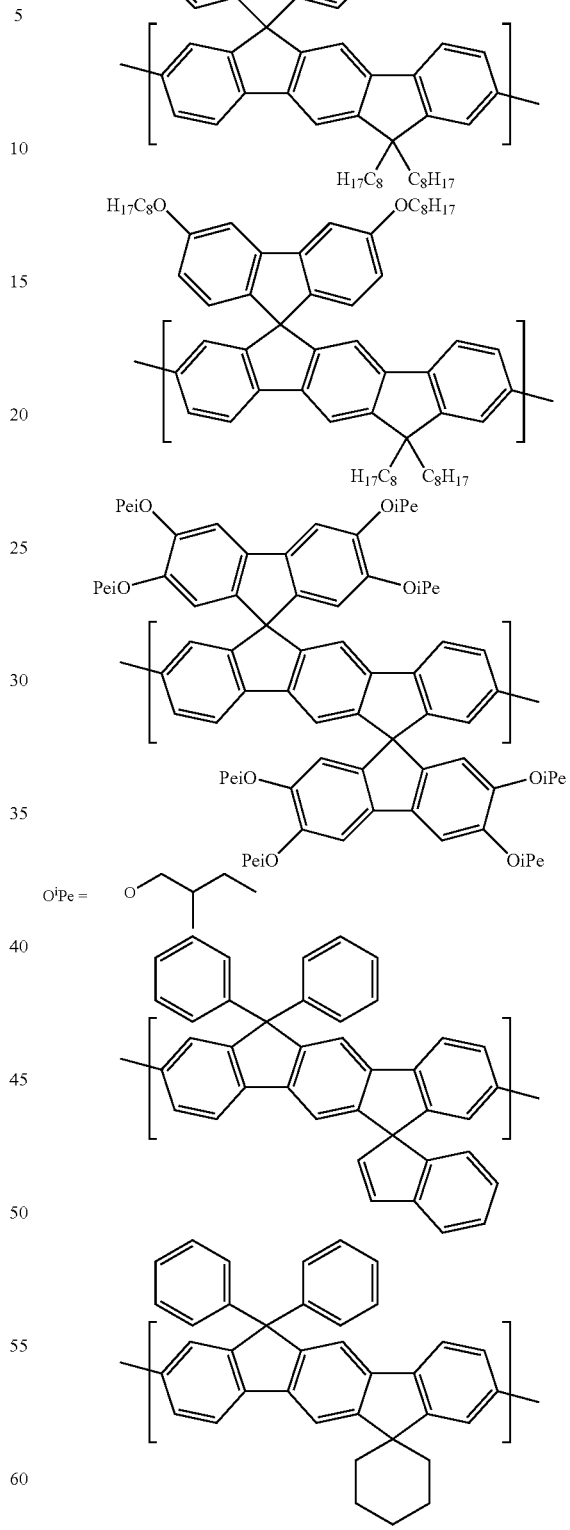

The monomers which may be polymerised to form the repeat units of the polymers of the present invention may be prepared according to any suitable method. Preferred methods for the preparation of monomers of the invention such as tetraaryl trans-indenofluorenes, dialkyl diary trans-indenofluorenes, alkyl triaryl trans-indenofluorenes and trialkyl aryl trans-indenofluorenes are now described.

material from which a wide variety of tetraaryl substituted trans-indenofluorenes may be prepared. Compound 3a is reacted with four equivalents of a metallated aromatic com-

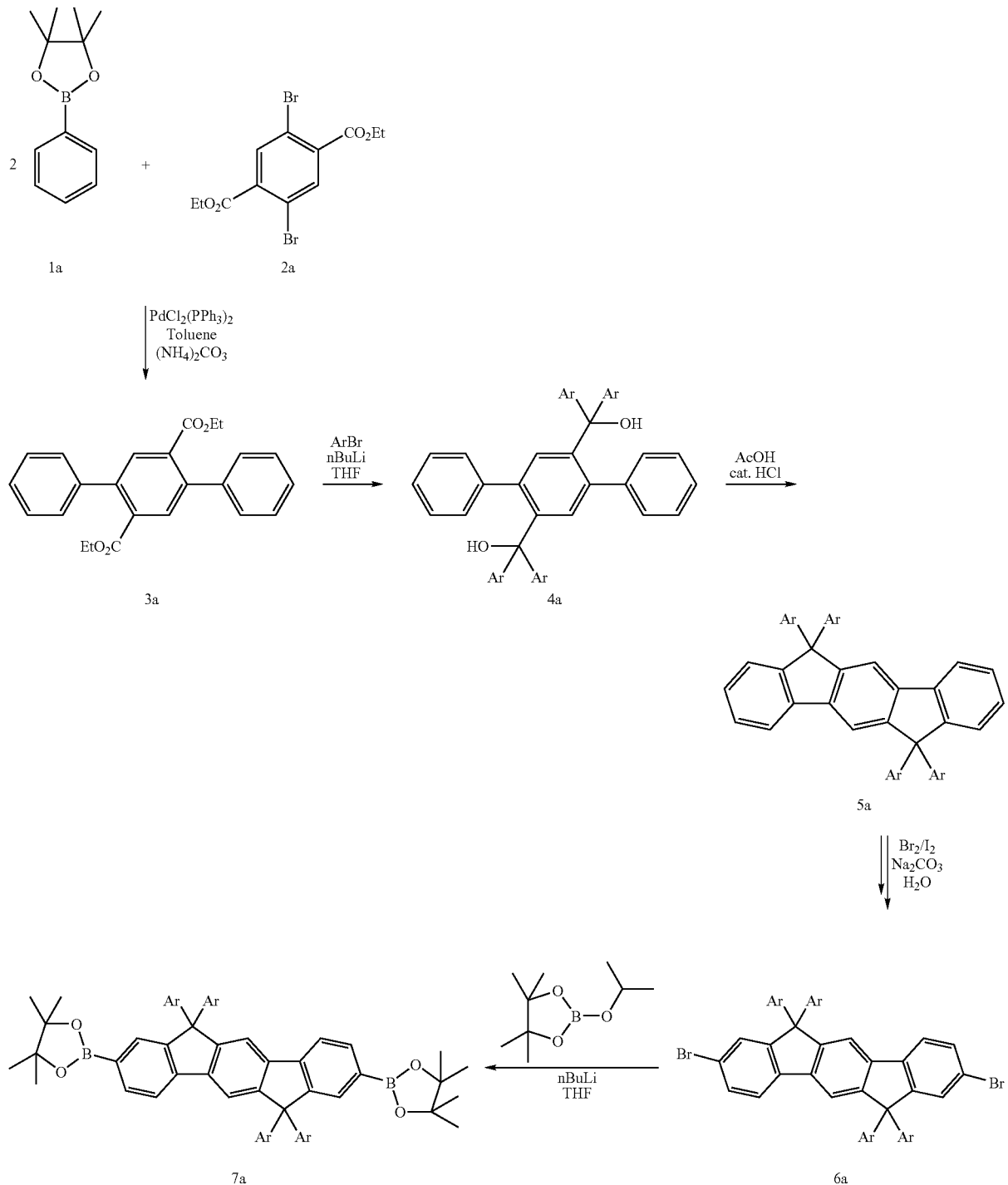

Scheme 1

Scheme 1 illustrates a method for the preparation of a tetraaryl substituted monomer. Two equivalents of boronic ester 1a are coupled to dibromo aromatic compound 2a by Suzuki coupling using a palladium catalyst and a tetraethylammonium carbonate base. Compound 3a forms the starting pound forming intermediate 4a which is heated in glacial acetic acid in the presence of HCl to form the tetraaryl substituted trans-indenofluorene 5a. In order to prepare monomers suitable to undergo Suzuki or Yamamoto coupling the compound 5a is brominated. The dibrominated compound 6a may be further reacted with a boronic ester to form a boronic diester 7a.

Scheme 2 below illustrates the preparation of a dialkyl diaryl substituted trans-indenofluorene.

trans-indenofluorene may be further reacted to form the polymerisable compounds 6b and 7b.

Scheme 2 illustrates a method for the formation of a dialkyl diaryl trans-indenofluorene; in order to prepare, for example,

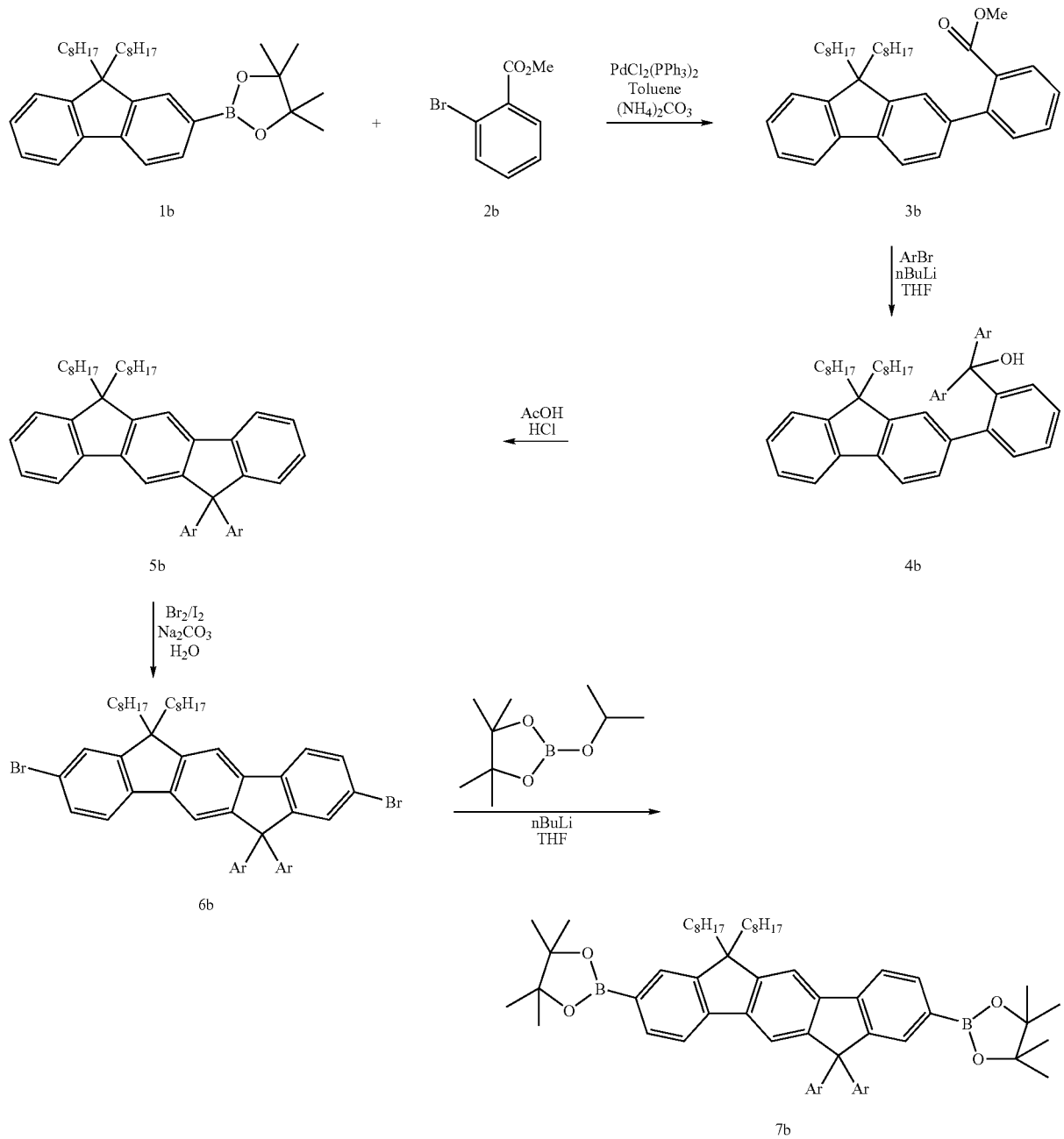

The boronic ester of a suitably substituted fluorene is prepared, in Scheme 2 the fluorene 1b is a 9,9-dioctylfluorene. The boronic ester 1b undergoes Suzuki coupling with a 2-bromobenzoate 2b to form the terphenyl compound 3b. The terphenyl compound 3b is then reacted with two equivalents of a metallated aromatic compound to form intermediate 4b. Intermediate 4b is heated in glacial acetic acid to form the dialkyl diaryl trans-indenofluorene 5b. The dialkyl diaryl trans-indenofluorene may be further reacted to form the polymerisable compounds 6b and 7b.

alkyl triaryl trans-indenofluorenes or trialkyl aryl trans-indenofluorenes it is necessary that the starting compound 1b comprises a 9,9-unsymmetrically substituted fluorene. Suitable 9,9-unsymmetrically substituted fluorenes are disclosed in WO 00/22026 and DE 19846767. Scheme 3 below illustrates a method of forming monomers according to the invention wherein arylene substituents of the monomer are present in the starting material.

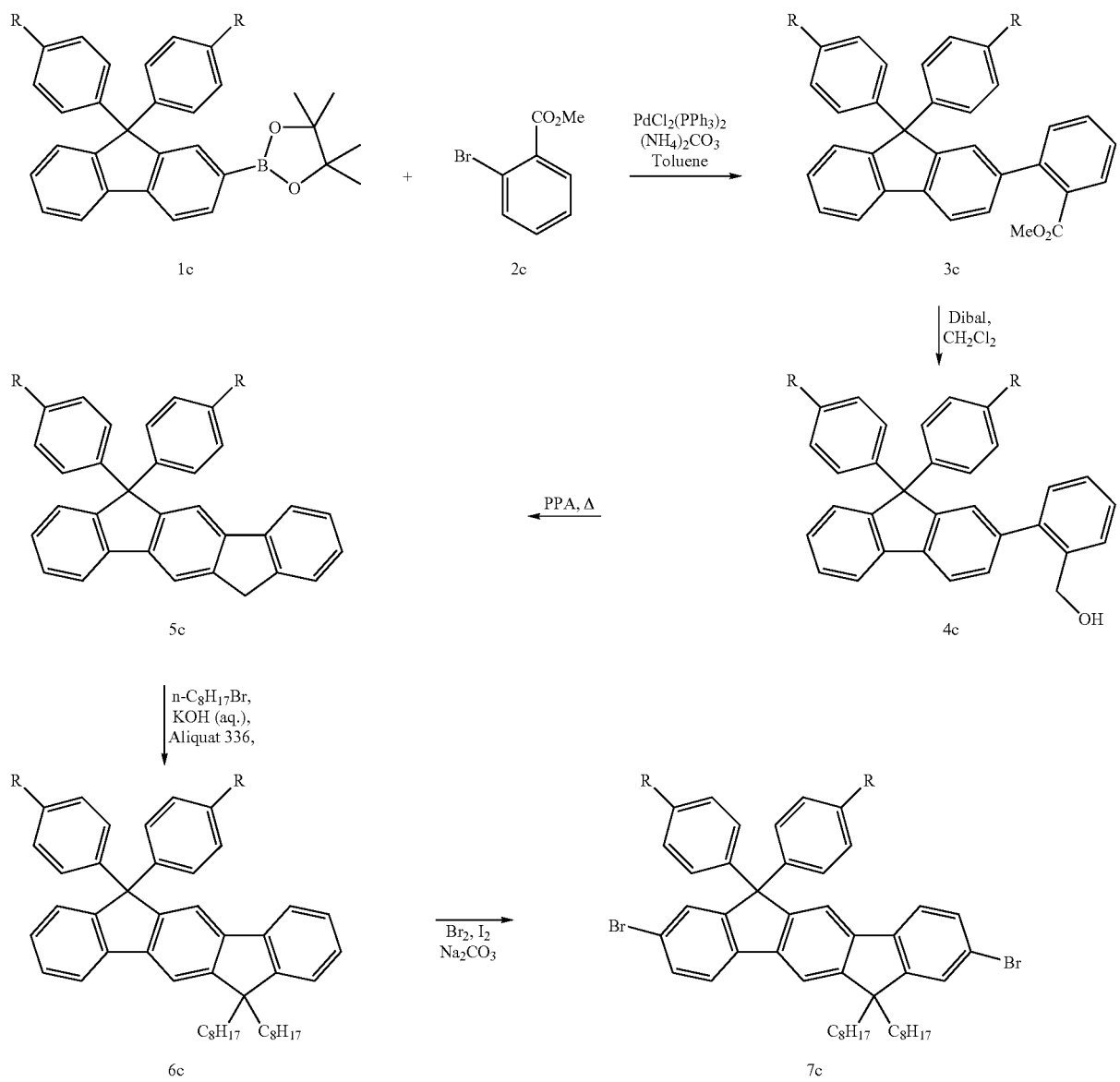
R in Scheme 3 represents a substituent. Where R is hydrogen, the above route may result in halogenation of the 4-position of the phenyl (or other aryl) substituent. Scheme 4 illustrates such a route.
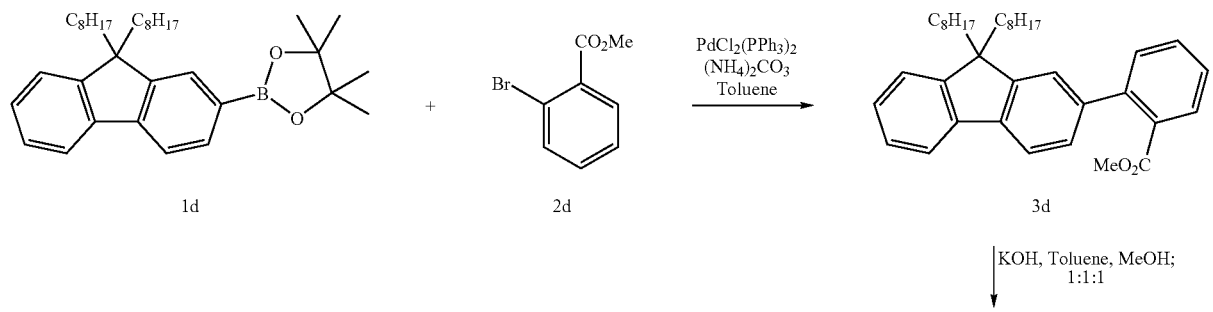

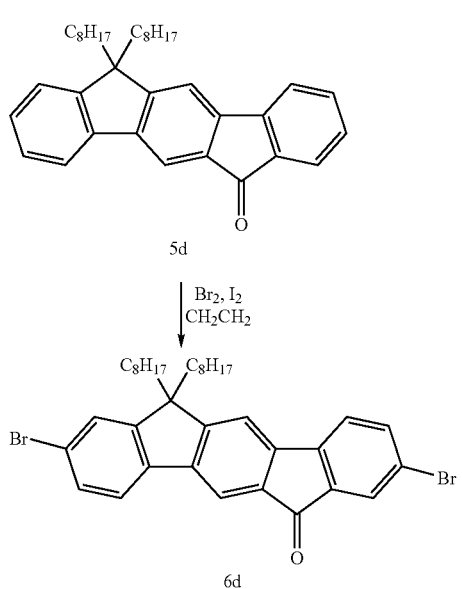

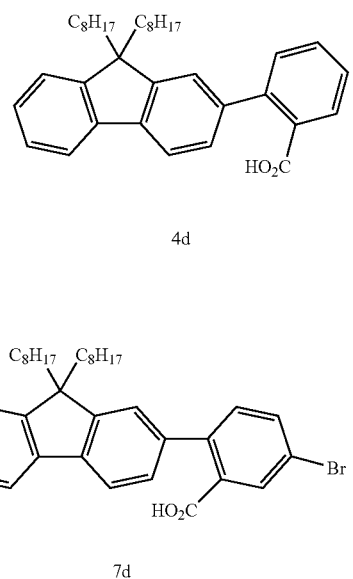

The polymers of the present invention may be homopolymers or copolymers. The use of monomers with different electronic properties in copolymers allows a greater degree of control over the electronic and light emissive properties of the polymer.

A wide range of comonomers for polymerisation with the monomers of the invention will be apparent to the skilled person. One class of co-repeat units is arylene repeat units, in particular: 1,4-phenylene repeat units as disclosed in J. Appl. Phys. 1996, 79, 934; fluorene repeat units as disclosed in EP 0842208, trans-indenofluorene repeat units as disclosed in, for example, Macromolecules 2000, 33(6), 2016-2020; spirobifluorene repeat units as disclosed in, for example EP 0707020; and stilbene repeat units (commonly known as "OPV" repeat units) as disclosed in WO 03/020790. Each of these repeat units is optionally substituted. Examples of substituents include solubilising groups such as $C_{1-20}$alkyl or alkoxy; electron withdrawing groups such as fluorine, nitro or cyano; and substituents for increasing glass transition temperature (Tg) of the polymer such as bulky groups, e.g. tert-butyl or optionally substituted aryl groups.

Further examples of comonomers include triarylamines as disclosed in, for example, WO 99/54385 and heteroaryl units as disclosed in, for example, WO 00/46321 and WO 00/55927.

Particularly preferred triarylamine repeat units for such copolymers include units of formulae 1-6:

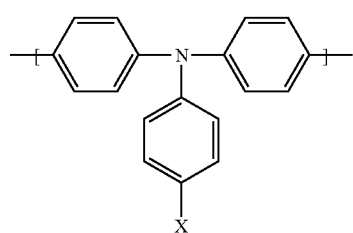

1

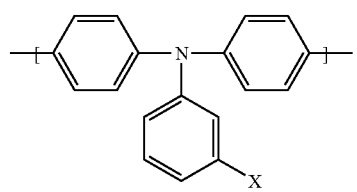

2

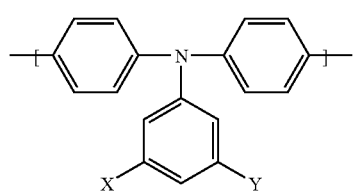

3

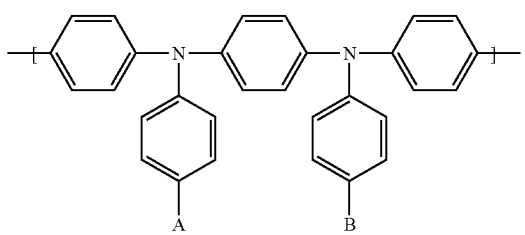

4

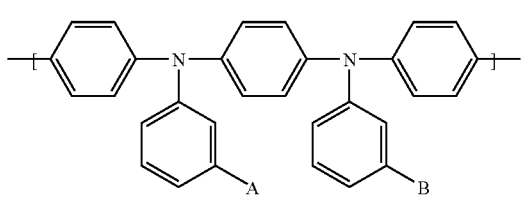

5

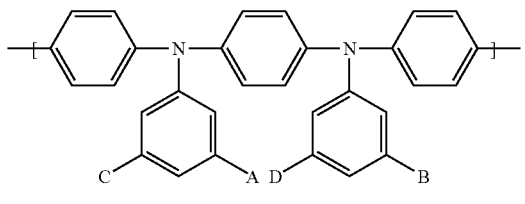

6

X and Y may be the same or different and are substituent groups. A, B, C and D may be the same or different and are substituent groups. It is preferred that one or more of X, Y, A, B, C and D is independently selected from the group consisting of alkyl, aryl, perfluoroalkyl, thioalkyl, cyano, alkoxy, heteroaryl, alkylaryl and arylalkyl groups. One or more of X, Y, A, B, C and D also may be hydrogen. It is preferred that one or more of X, Y, A, B, C and D is independently an unsubstituted isobutyl group, an n-alkyl, an n-alkoxy or a trifluoromethyl group because they are suitable for helping to select the HOMO level and/or for improving solubility of the polymer.

Particularly preferred heteroaryl repeat units for such copolymers include units of formulae 7-21:

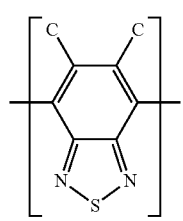

7 wherein $R_6$ and $R_7$ are the same or different and are each independently a substituent group. Preferably, one or both of $R_6$ and $R_7$ may be selected from hydrogen, alkyl, aryl, perfluoroalkyl, thioalkyl, cyano, alkoxy, heteroaryl, alkylaryl, or arylalkyl. These groups are preferred for the same reasons as discussed in relation to X, Y, A, B, C and D above. Preferably, for ease of manufacture, $R_6$ and $R_7$ are the same. More preferably, they are the same and are each hydrogen or a phenyl group.

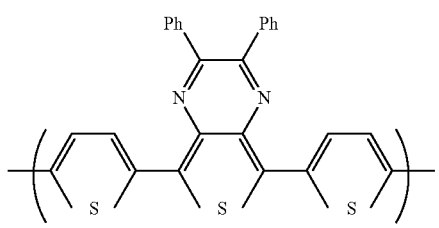

8

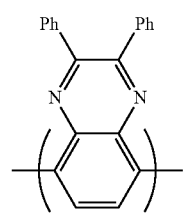

9

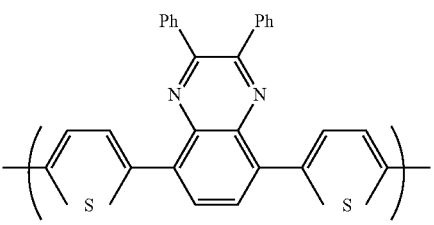

10

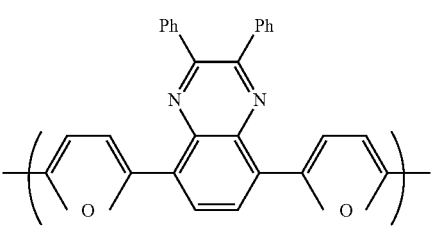

11

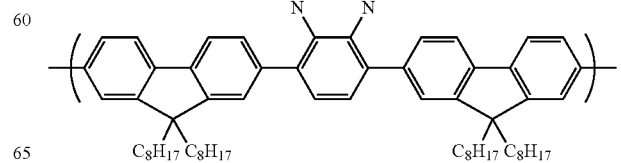

12

13
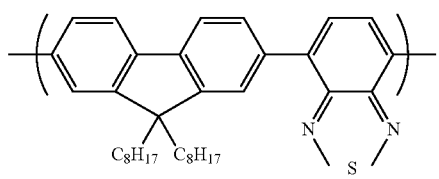

14
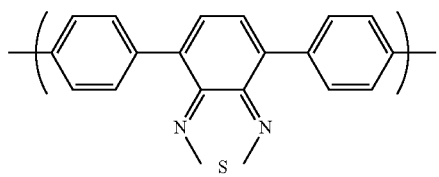

15
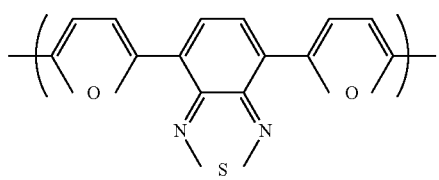

16
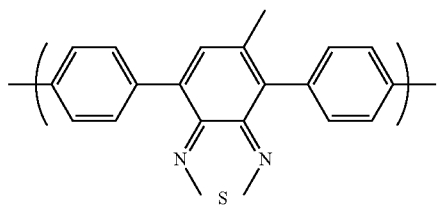

17
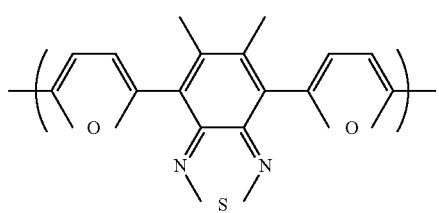

18
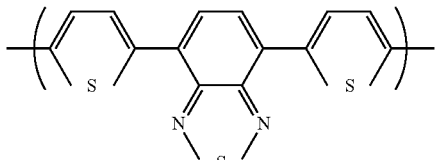

19
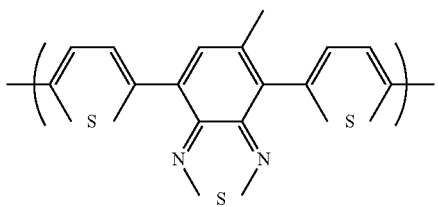

20
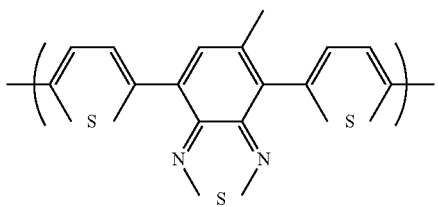

21
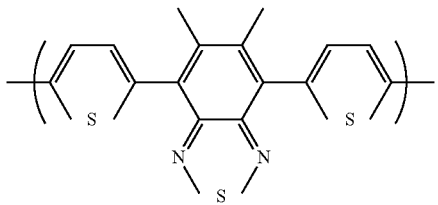

The trans-indenofluorene repeat units of the present invention can act as efficient electron transporting units and light emitting units. It is therefore beneficial to combine the aryl substituted trans-indenofluorenes with hole transporting moieties such as triarylamines to provide polymers having electron and hole transporting and light emitting properties. A particularly useful example of such a polymer is the copolymer of a dialkyl diaryl trans-indenofluorene, TA and BTA shown below.

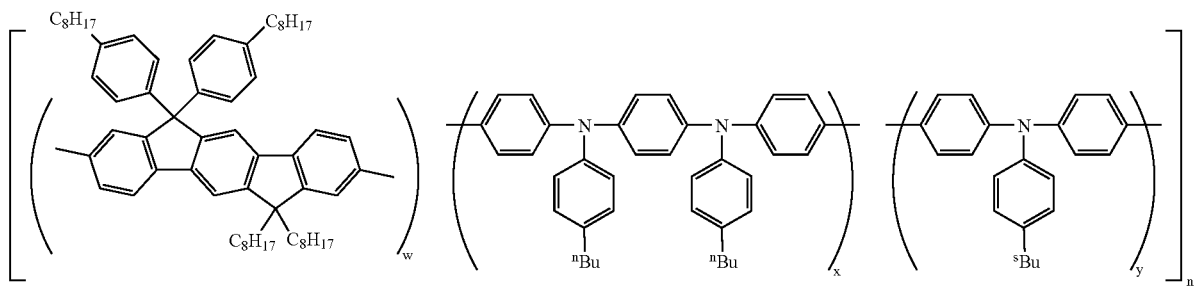

wherein w+x+y=1, w≥0.5, 0≤x+y≤0.5 and n≥2.

The polymers of the present invention are prepared by the polymerisation of monomers of formula (II):

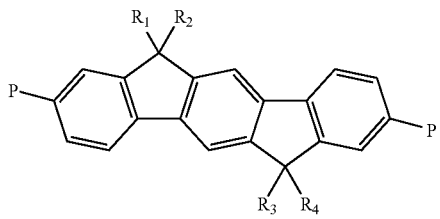

(II)

where P is a polymerisable group. Preferably P is a boron derivative group such as a boronic ester or a reactive halide such as bromine.

Preferred methods for polymerisation of these monomers are Suzuki polymerisation as described in, for example, WO 00/53656 and Yamamoto polymerisation as described in, for example, T. Yamamoto, "Electrically Conducting And Thermally Stable pi-Conjugated Poly(arylene)s Prepared by Organometallic Processes", Progress in Polymer Science 1993, 17, 1153-1205 or DE 10241814.4, or Stille coupling. For example, in the synthesis of a linear polymer by Yamamoto polymerisation, a monomer having two reactive halide groups P is used. Similarly, according to the method of Suzuki polymerisation, at least one reactive group P is a boron derivative group.

Suzuki polymerisation may be used to prepare regioregular, block and random copolymers. In particular, random copolymers may be prepared when one reactive group P is a halogen and the other reactive group P is a boron derivative group. Alternatively, block or regioregular, in particular AB, copolymers may be prepared when both reactive groups of a first monomer are boron and both reactive groups of a second monomer are halide. The synthesis of polymers with blocky structures is described in detail in, for example, DE 103 37 077.3. Suzuki polymerisation employs a Pd(0) complex or a Pd(II) salt. Preferred Pd(0) complexes are those bearing at least one phosphine ligand such as $Pd(Ph_3P)_4$. Another preferred phosphine ligand is tris(orthotolyl)phosphine, i.e. $Pd(o-Tol)_4$. Preferred Pd(II) salts include palladium acetate, i.e. $Pd(OAc)_2$. Suzuki polymerisation is performed in the presence of a base, for example sodium carbonate, potassium phosphate or an organic base such as tetraethylammonium carbonate.

Yamamoto polymerisation employs a Ni(0) complex, for example bis(1,5-cyclooctadienyl) nickel(0).

As alternatives to halogens as described above, leaving groups of formula —O—$SO_2$Z can be used wherein Z is as described above. Particular examples of such leaving groups are tosylate, mesylate and triflate.

The aryl substituted poly(trans-indenofluorenes) of the present invention have particular application in optical devices, in particular organic light emitting devices. Organic light emitting devices comprise a layered structure comprising a lower electrode situated on a substrate for injection of charge carriers of a first type, an upper electrode for injection of charge carriers of a second type and a layer of organic light emitting material located between the lower and upper electrodes. Additionally, charge transporting layers of organic material may also be located between the electrodes. When a voltage is supplied across the electrode of the device opposite charge carriers, namely electrons and holes, are injected into the organic light emitting material. The electrons and holes recombine in the layer of organic light emitting material resulting in the emission of light. One of the electrodes, the anode, comprises a high work function material suitable for injecting holes into the layer of organic light emitting material, this material typically has a work function of greater than 4.3 eV and may be selected from the group comprising indium-tin oxide (ITO), tin oxide, aluminum or indium doped zinc oxide, magnesium-indium oxide, cadmium tin-oxide, gold, silver, nickel, palladium and platinum. The anode material is deposited by sputtering or vapour deposition as appropriate.

The other electrode, the cathode, comprises a low work function material suitable for injecting electrons into the layer of the organic light emitting material. The low work function material typically has a work function of less than 3.5 eV and may be selected from the group including Li, Na, K, Rb, Be, Mg, Ca, Sr, Ba, Yb, Sm and Al. The cathode may comprise an alloy of such metals or an alloy of such metals in combination with other metals, for example the alloys MgAg and LiAl. The cathode preferably comprises multiple layers, for example Ca/Al, Ba/Al or LiAl/Al. The device may further comprise a layer of dielectric material between the cathode and the emitting layer, such as is disclosed in WO 97/42666. In particular it is preferred to use an alkali or alkaline earth metal fluoride as a dielectric layer between the cathode and the emitting material. A particularly preferred cathode comprises LiF/Ca/Al, with a layer of LiF of thickness from 1 to 10 nm, a layer of Ca of thickness of 1 to 25 nm and a layer of Al of thickness 10 to 500 nm. Alternatively a cathode comprising $BaF_2$/Ca/Al may be used. The cathode materials are deposited by vacuum deposition.

For light emission to occur from the device it is preferred that either the cathode, the anode or both are transparent or semi-transparent. Suitable materials for transparent anodes include ITO and thin layers of metals such as platinum. Suitable materials for transparent cathodes include a thin layer of electron injecting material in proximity to the layer of organic light emitting material and a thicker layer of transparent conductive material overlying the layer of electron injecting material e.g. a cathode structure comprising Ca/Au. Where neither the cathode nor the anode is transparent or semi-transparent light emission occurs through the edge of the device. It will be appreciated that such transparency is not a requirement where the polymers of the invention are used in switching devices.

The polymers of the present invention may comprise the light emissive layer of the device or may comprise an electron transport layer of the device. The polymers may be deposited by any suitable method although solution deposition methods are preferred. Solution deposition techniques include spin-coating, dip-coating, doctor blade coating, screen printing, flexographic printing and ink-jet printing. Ink-jet printing is particularly preferred as it allows high resolution displays to be prepared.

The organic light emitting device may include further organic layers between the anode and cathode to improve charge injection and device efficiency. In particular a layer of hole-transporting material may be situated over the anode. The hole-transport material serves to increase charge conduction through the device. The preferred hole-transport material used in the art is the conductive organic polymer polystyrene sulfonic acid doped poly(ethylene dioxythiophene) (PEDOT: PSS) as disclosed in WO 98/05187. Other hole transporting materials such as doped polyaniline or TPD (N,N'-diphenyl-N,N'-bis(3-methylphenyl)[1,1'-biphenyl]-4,4'-diamine) may also be used. A layer of electron transporting or hole blocking material may be positioned between the layer of light emitting material and the cathode if required to improve device efficiency.

The substrate of the organic light emitting device should provide mechanical stability to the device and act as a barrier to seal the device from the environment. Where it is desired that light enter or leave the device through the substrate, the substrate should be transparent or semi-transparent. Glass is widely used as a substrate due to its excellent barrier properties and transparency. Other suitable substrates include ceramics, as disclosed in WO 02/23579 and plastics such as acrylic resins, polycarbonate resins, polyester resins, polyethylene terephthalate resins and cyclic olefin resins. Plastic substrates may require a barrier coating to ensure that they remain impermeable. The substrate may comprise a composite material such as the glass and plastic composite disclosed in EP 0949850.

The organic light emitting device is provided with an encapsulation means which acts to seal the device from the atmosphere. Suitable methods of encapsulation include covering the device on the cathode side with a metal can or glass sheet or providing an impermeable film over the device, such as a film comprising a stack of polymer layers and inorganic layers.

The invention is further described by means of the following examples.

EXAMPLES

Monomer Synthesis

Synthesis of phenylboronic acid pinacol ester 1a

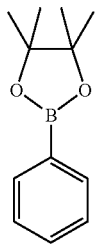

1a

Phenyl boronic acid (100 g, 0.82 mol, 1 equiv.) and pinacol (96.92 g, 0.82 mol, 1 equiv.) were dissolved in toluene (500 mL) at room temperature. The cloudy solution was then placed on to a rotary evaporator and stirred for 2 hours at 60° C. After this period the solid had dissolved, concurrent with the formation of water (ca. 29.5 mL) as a second layer. The water was then removed in a separating funnel and the crude reaction filtered through Celite. Evaporation of the solvent yielded a clear pale yellow oil which solidified on cooling in a refrigerator to give the title compound in a near-quantitative yield as a white solid (ca. 167 g).

Synthesis of 2,5-diphenyl-terephthalic acid diethylester 3a

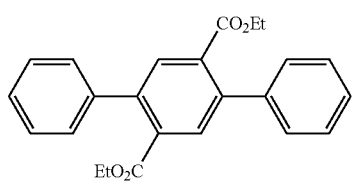

3a

To a 3 L 3-neck flask equipped with a mechanical stirrer, reflux condenser and rubber septum was added phenyl boronic acid pinacol ester 2a (128.9 g, 0.63 mol, 2 equiv.) and 2,5-dibromo-terephthalic acid diethylester 1a (120 g, 0.32 mol, 1 equiv.) as a suspension in toluene (500 mL). A further 500 mL of toluene was then added and the reaction mixture briefly stirred before degassing using a nitrogen purge for 1 hour at 40° C. After this period dichloro-bis(triphenyl phosphine) palladium (II) (0.55 g, 0.78 mmol, 1/8 mol % per bromide) was added as a dry powder. The reaction mixture was then stirred under nitrogen for 15 minutes at 40° C. before the addition of tetra-ethylammonium carbonate (790 mL, ca. 33 wt % aqueous solution, 2 equiv. per arylboronate). The reaction was then stirred at 90° C. under nitrogen overnight (ca. 16 hrs.). TLC analysis at this point (DCM, silica plates) revealed a bright fluorescent blue spot (Rf ca. 0.6) and the absence of any starting material. Once the reaction mixture had cooled the aqueous layer was extracted and the solvent removed under reduced pressure to yield a light brown solid residue which was recrystallised from methanol to give the title compound as white crystalline solid. Slow evaporation of the mother liquor provided a second crop of product (92 g total, 77%, >99% pure by GC).

The radicals Aryl and Ar as used in formulae 4a, 5a, 6a, 7a, 4b, 5b, 6b, 7b, denote 4-(n-octyl)phenyl.

Synthesis of 2',5'-bis(di(4-octylphenyl)hydroxymethyl)-1,1',4',1"-terphenyl 4a

Bromo-4-octyl-benzene (4 equivs.) was dissolved in anhydrous tetrahydrofuran

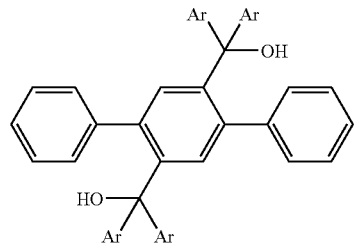

4a (THF) at −78° C. nBuLi (4 equivs., 2.5 M in hexanes) was then slowly added via a pressure equalised dropping funnel. After the addition the reaction was stirred for 30 minutes to insure complete transmetallation. 2,5-diphenyl-terephthalic acid diethylester 3a (1 equiv.) was then slowly added as a solution in THF. The temperature was maintained at −78° C. throughout the operation. After a further 30 minutes the reaction was allowed to warm up to room temperature and stirring was continued over night (ca. 16 hours). After this period water was added to destroy any unreacted butyl lithium and the THF removed under reduced pressure. The crude reaction mixture was extracted into dichloromethane (DCM) and purified by trituration from methanol.

Synthesis of 6,6,12,12-tetrakis-(4-octylphenyl)indeno[1,2-b]fluorene 5a

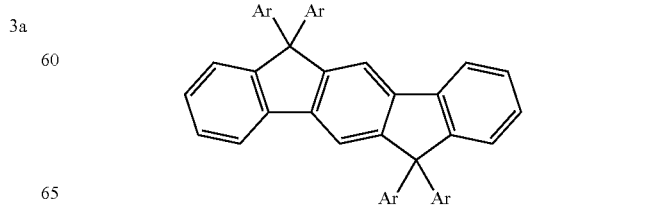

5a

The arylated precursor 4a was heated in a mixture of glacial acetic acid and concentrated hydrochloric acid (a few drops) over night. After this period the reaction mixture was allowed to cool to room temperature before precipitation into a large excess of rapidly stirred water. The crude product was collected by filtration and purified by crystallisation.

Synthesis of 2,8-dibromo-6,6,12,12-tetrakis-(4-octylphenyl)indeno[1,2-b]fluorene 6a

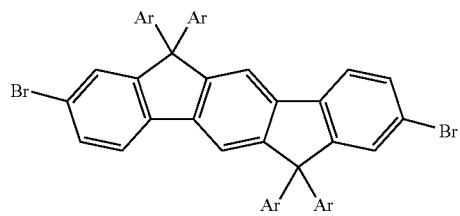

Compound 5a was treated with an iodine/bromine mixture, as described in WO 00/55927.

Synthesis of 2,8-bis(boronic acid pinacol ester)-6,6,12,12-tetrakis-(4-octylphenyl)indeno[1,2-b]fluorene 7a

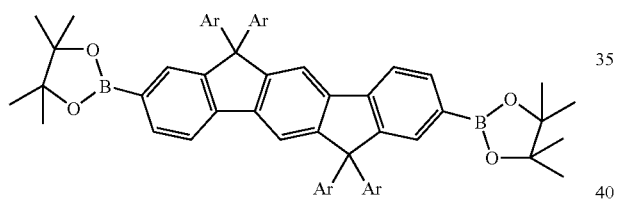

The title compound was prepared from compound 6a according to standard procedures as described in, for example, WO 00/55927.

Synthesis of 2-(2-methyl benzoate)-9,9-dioctylfluorene 3b

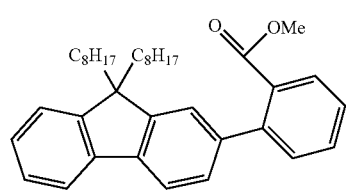

To a 3 L 3-neck flask equipped with a mechanical stirrer, reflux condenser and rubber septum was added 2-(boronic acid pinacol ester)-9,9-dioctylfluorene 1b (10 g, 21.72 mmol, 1 equiv.) and 2-bromo methyl benzoate 2b (4.67 g, 21.72 mmol, 1 equiv.) dissolved in toluene (100 mL) at room temperature. The solution was degassed using a nitrogen purge for 1 hour before dichloro bis(triphenyl phosphine) palladium (II) (20 mg, 0.027 mmol, 1/8 mol % per bromide) was added as a dry powder. The reaction mixture was then stirred under nitrogen for 15 minutes before the addition of tetra-ethylammonium carbonate (25 mL, ca. 33 wt % aqueous solution, 2 equiv. per arylboronate). The reaction was then stirred at 90° C. under nitrogen overnight (ca. 16 hrs.). TLC analysis at this point (DCM, silica plates) revealed a bright fluorescent blue spot (Rf ca. 0.6) and the absence of any starting material. Once the reaction mixture had cooled the aqueous layer was extracted and the solvent removed under reduced pressure to yield a yellow oil which was purified by recrystallisation to give the title compound.

Synthesis of 2-[phenyl-2-(diarylhydroxymethyl)]-9,9-dioctylfluorene 4b

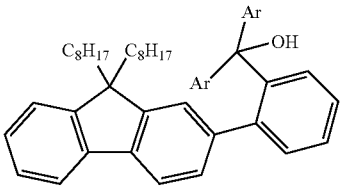

Compound 4b was prepared in an analogous manner to compound 4a.

Synthesis of 6,6-dioctyl-12,12-bis(4-octylphenyl)indeno[1,2b]fluorene 5b

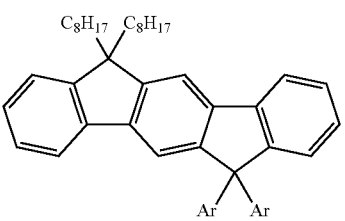

Compound 5b was prepared in an analogous manner to compound 5a.

Synthesis of 2,8-dibromo-6,6-dioctyl-12,12-bis(4-octylphenyl)indeno[1,2-b]fluorene 6b

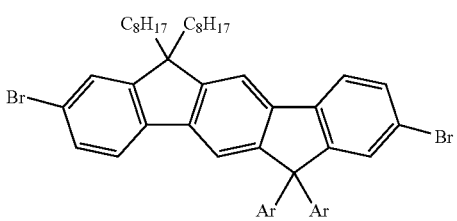

Compound 6b was prepared in an analogous manner to compound 6a.

Synthesis of 2,8-bis(phenylboronic acid pinacol ester)-6,6-dioctyl-12,12-bis(4-octylphenyl)indeno[1,2-b]fluorene 7b Compound 7b was prepared in an analogous manner to compound 7a.

Polymer Synthesis

Polymers according to the invention were prepared by Suzuki polymerisation of boronic acid diesters of aryl substituted indenofluorenes as described above with dibromo-arylamines according to the method described in WO 00/53656. For the purpose of comparison, identical polymers were prepared wherein substituents $R_1$-$R_4$ of formula (I) above are all n-octyl.

Polymer 1 has a Tg of 240° C. In contrast, the corresponding polymer comprising tetra(n-octyl)indenofluorene has a Tg of 167° C. The higher Tg is beneficial for the use of the polymer in light emitting diodes and results in more stable blue emission.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:

1. A polymer comprising optionally substituted first repeat units of formula (I):

wherein
* indicates the position that formula (I) is bonded to the polymer chain,
wherein $R_1$, $R_2$, $R_3$ and $R_4$ are selected from alkyl, alkyloxy, aryl, aryloxy, heteroaryl or heteroaryloxy groups, and $R_1$ and $R_2$ and/or $R_3$ and $R_4$ may be linked to form a monocyclic or polycyclic, aliphatic or aromatic ring system, provided that at least one of $R_1$, $R_2$, $R_3$ and $R_4$ is an aryl group.

2. A polymer according to claim 1 wherein at least two of $R_1$, $R_2$, $R_3$ and $R_4$ are an aryl group.

3. A polymer according to claim 2 wherein said aryl group is a 4-octylphenyl group or a 4-tert-butyl-phenyl group.

4. A polymer according to claim 1 wherein at least three of $R_1$, $R_2$, $R_3$ and $R_4$ are an aryl group.

5. A polymer according to claim 1 wherein $R_1$, $R_2$, $R_3$ and $R_4$ are an aryl group.

6. A polymer according to claim 1 wherein $R_1$ and $R_2$ are an aryl group and $R_3$ and $R_4$ are an alkyl group.

7. A polymer according to claim 6, wherein said aryl group is an optionally substituted phenyl group.

8. A polymer according to claim 1 comprising a second repeat unit.

9. A polymer according to claim 8 wherein said second repeat unit is selected from the group consisting of triarylamines and heteroaromatics.

10. A switching device comprising the polymer according to claim 9.

11. An organic light emitting device comprising the polymer according to claim 1.

12. A field effect transistor comprising an insulator having a first side and a second side; a gate electrode located on the first side of the insulator; a polymer according to claim 1 located on the second side of the insulator; and a drain electrode and a source electrode located on the polymer.

13. An integrated circuit comprising a field effect transistor according to claim 12.

14. A photovoltaic cell comprising a polymer according to claim 1.

15. A polymer according to claim 1, wherein $R_1$, $R_2$, $R_3$ and $R_4$ are alkyl or aryl and wherein two or four of $R_1$, $R_2$, $R_3$ and $R_4$ are aryl.

16. A polymer according to claim 15, wherein said aryl is a substituted aryl.

17. A polymer according to claim 15, wherein said aryl is a substituted phenyl.

18. A polymer according to claim 15, wherein said aryl is a 4-tert-butyl-phenyl group.

* * * * *